United States Patent
Wulff et al.

(10) Patent No.: US 7,145,034 B2
(45) Date of Patent: Dec. 5, 2006

(54) METHOD FOR PRODUCING N-PHOSPHONOMETHYLGLYCINE

(75) Inventors: Christian Wulff, Mannheim (DE); Stefan Orsten, Ellerstadt (DE); Alfred Oftring, Bad Dürkheim (DE); Peter Zehner, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 114 days.

(21) Appl. No.: 10/481,579

(22) PCT Filed: Jun. 21, 2002

(86) PCT No.: PCT/EP02/06902

§ 371 (c)(1),
(2), (4) Date: Dec. 22, 2003

(87) PCT Pub. No.: WO03/000703

PCT Pub. Date: Jan. 3, 2003

(65) Prior Publication Data

US 2004/0236145 A1    Nov. 25, 2004

(30) Foreign Application Priority Data

Jun. 22, 2001    (DE) ................ 101 30 135

(51) Int. Cl.
*C07F 9/22* (2006.01)
*C07F 9/28* (2006.01)

(52) U.S. Cl. .............. 562/18; 562/8; 562/17; 562/24; 558/144; 558/137

(58) Field of Classification Search .......... 562/24, 562/8, 17, 18; 558/144, 137
See application file for complete search history.

(56) References Cited

U.S. PATENT DOCUMENTS

| | | |
|---|---|---|
| 2,823,222 A | 2/1958 | Sexton et al. |
| 3,923,877 A | 12/1975 | Barton |
| 4,008,296 A | 2/1977 | Barton |
| 4,053,505 A | 10/1977 | Dutra |
| 4,065,491 A | 12/1977 | Pfliegel et al. |
| 4,067,719 A | 1/1978 | Dutra |
| 4,083,898 A | 4/1978 | Dutra |
| 4,089,671 A | 5/1978 | Dutra |
| 4,181,800 A | 1/1980 | Kamiya et al. |
| 4,304,718 A | 12/1981 | Kamiya et al. |
| 4,415,503 A | 11/1983 | Robbins |
| 4,428,888 A | 1/1984 | Robbins |
| 4,429,124 A | 1/1984 | Felix |
| 4,442,044 A * | 4/1984 | Purdum .............. 558/126 |
| 4,454,063 A | 6/1984 | Felix |
| 4,487,724 A | 12/1984 | Felix |
| 5,053,529 A | 10/1991 | Ha et al. |
| 6,660,878 B1 | 12/2003 | Wulff et al. |
| 2003/0004370 A1 | 1/2003 | Wulff et al. |

FOREIGN PATENT DOCUMENTS

| | | |
|---|---|---|
| DE | 118 435 | 6/1975 |
| DE | 141 929 | * 5/1980 |
| EP | 0 097 522 | 1/1984 |
| EP | 0 104 775 | 4/1984 |
| EP | 0 149 294 | 7/1985 |
| EP | 0 164 923 | 12/1985 |

* cited by examiner

*Primary Examiner*—Thurman K. Page
*Assistant Examiner*—Chukwuma Nwaonicha
(74) *Attorney, Agent, or Firm*—Novak Druce & Quigg, LLP

(57) ABSTRACT

The invention relates to a process for preparing N-phosphono-methylglycine by reacting a hexahydrotriazine compound with a triacyl phosphite in an organic solvent, hydrolyzing the resulting phosphono compound after prior extraction into an aqueous phase and separation from the organic phase. The process avoids decomposition of the organic solvent during hydrolysis.

14 Claims, No Drawings

METHOD FOR PRODUCING N-PHOSPHONOMETHYLGLYCINE

The invention relates to a process for preparing N-phosphono-methylglycine by reacting a hexahydrotriazine compound with a triacyl phosphite in an organic solvent and hydrolyzing the resulting phosphono compound after prior extraction into an aqueous phase and separation from the organic phase.

N-Phosphonomethylglycine (glyphosate) is a total herbicide which is widely used. Numerous processes for preparing phosphonomethyl-glycine are known. One possible preparation is to react hexahydrotriazine derivatives with phosphorous esters. Thus, U.S. Pat. No. 4,181,800 describes the preparation of hexahydrotriazines of the formula:

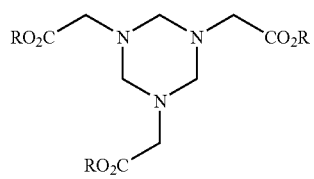

5 and U.S. Pat. No. 4,053,505 describes the reaction of these hexahydro-triazines with phosphorous diesters and subsequent hydrolysis of the resulting product to give phosphonomethylglycine. It has been found that there is scope for improving both the yield and the selectivity for the monophosphonated product. Moreover, phosphorous diesters are very expensive.

EP-A-104 775 (corresponding to U.S. Pat. Nos. 4,425,284, 4,482,504 and 4,535,181) describes the reaction of the above hexahydro-triazines with an acyl halide and the subsequent phosphonation with a phosphorous triester and hydrolysis to give phosphono-methyl glycine, in accordance with the following equation:

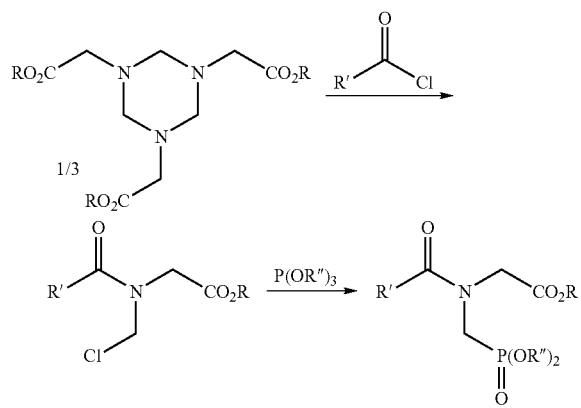

In this manner, phosphonomethylglycine is indeed obtained in a relatively good yield; however, in addition to the use of the expensive phosphorous ester, the process furthermore requires the use of a carbonyl chloride. Moreover, the carbonyl chloride can, if at all, only be recovered in the form of the free acid, which then has to be reconverted into the acid chloride in a separate step, resulting in a considerable increase of the costs of the process. Furthermore, it is not possible to recycle all of the alcohol used to esterify the phosphorous acid, since during the reaction one equivalent of the corresponding alkyl chloride is formed which is furthermore toxicologically objectionable.

U.S. Pat. No. 4,428,888 (corresponds to EP-A-149 294) describes the reaction of the hexahydrotriazine mentioned above with a phosphorous acid chloride in the presence of a strong anhydrous acid, for example hydrogen chloride, and a $C_1$–$C_6$-carboxylic acid, such as acetic acid. By this route, numerous undefined byproducts are obtained which lower the yield of phosphonomethylglycine and require a complicated purification of the product.

U.S. Pat. No. 4,442,044 describes the reaction of a hexahydrotriazine of the formula 5 with a phosphorous triester to give the corresponding phosphonate compound, which is used as herbicide.

DD-A-141 929 and DD-A-118 435 describe the reaction of an alkali metal salt of the above hexahydrotriazine (R=for example Na) with a phosphorous diester. However, owing to the poor solubility of the alkali metal salts, conversion is low.

U.S. Pat. No. 5,053,529 describes the preparation of phosphonomethylglycine by reacting the above hexahydrotriazines with phosphorous triesters in the presence of titanium tetrachloride, followed by hydrolysis of the resulting product. The use of titanium tetrachloride renders the preparation considerably more expensive. Moreover, the yields of phosphonomethylglycine are unsatisfactory.

U.S. Pat. Nos. 4,454,063, 4,487,724 and 4,429,124 describe the preparation of phosphonomethylglycine by reacting a compound of the formula

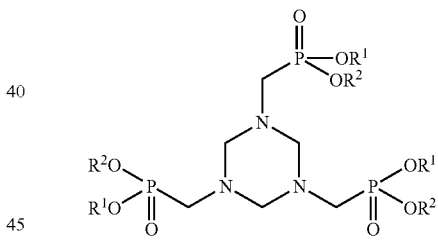

in which $R^1$ and $R^2$ are aromatic or aliphatic groups, with RCOX (X=Cl, Br, I) to give a compound of the formula

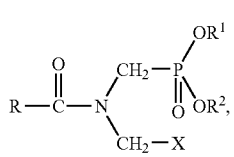

and reacting this compound with a metal cyanide and hydrolyzing the product obtained. The disadvantages of this process are as indicated above with respect to the use of the acid chloride.

Further synthesis possibilities are described starting from the cyanomethyl-substituted hexahydrotriazine of the formula

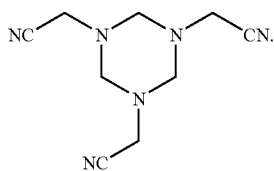

Thus, U.S. Pat. Nos. 3,923,877 and 4,008,296 disclose the reaction of this hexahydrotriazine derivative with a dialkyl phosphonate in the presence of an acid catalyst, such as hydrogen chloride, a Lewis acid, a carbonyl chloride or a carboxylic anhydride, to give a compound of the formula:

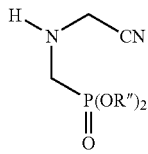

Subsequent hydrolysis affords phosphonomethylglycine, 8 to 10% of the diphosphonomethylated product resulting.

U.S. Pat. Nos. 4,067,719, 4,083,898, 4,089,671 and DE-A-2751631 describe the reaction of the cyanomethyl-substituted hexahydrotriazine with a diaryl phosphonate without catalyst to give a compound 9 where R″=aryl. This process has the same disadvantages as described above for the use of the carboxyl-substituted hexahydrotriazine 5.

EP-A-097 522 (corresponding to U.S. Pat. Nos. 4,476,063 and 4,534,902) describes the reaction of the hexahydrotriazine 6 with an acyl halide to give 10, subsequent phosphonation with a phosphorous triester or diester to give 11 and finally hydrolysis to phosphonomethylglycine according to the following reaction equation:

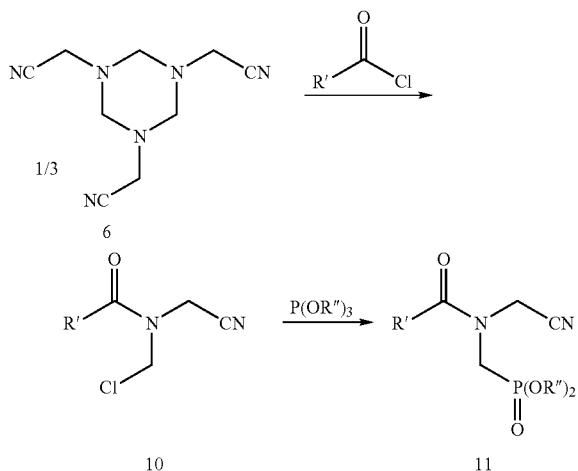

Here, too, the same disadvantages are observed as for the processes using carboxyl-substituted hexahydrotriazine derivatives.

Finally, U.S. Pat. No. 4,415,503 describes the reaction of the cyanomethyl-substituted hexahydrotriazine analogously to the process described in U.S. Pat. No. 4,428,888. In this case, too, the increased formation of byproducts is observed.

EP 164 923 A describes an improved hydrolysis of a compound of the formula 11.

DE 199 62 601 describes a process for preparing N-phosphono-methylglycine which comprises a) reacting a hexahydrotriazine derivative of the formula II

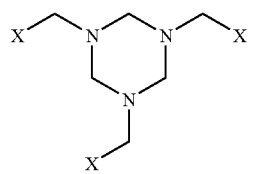

in which X is CN, COOZ, CONR$^1$R$^2$ or CH$_2$OY,

Y is H or a radical which is easily exchangeable for H;

Z is H, an alkali metal, an alkaline earth metal, C$_1$–C$_{18}$-alkyl or aryl which is unsubstituted or substituted by C$_1$–C$_4$-alkyl, NO$_2$ or OC$_1$–C$_4$-alkyl;

R$^1$ and R$^2$ may be identical or different and are H or C$_1$–C$_4$-alkyl, with a triacyl phosphite of the formula III

in which the radicals R$^3$, which may be identical or different, are C$_1$–C$_{18}$-alkyl or aryl which is unsubstituted or substituted by C$_1$–C$_4$-alkyl, NO$_2$ or OC$_1$–C$_4$-alkyl to give a compound of the formula I

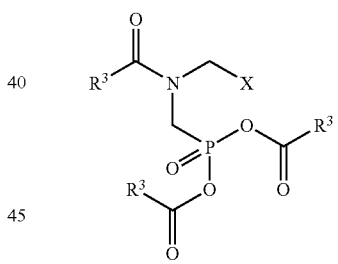

in which R$^3$ and X are as defined above, and b) hydrolyzing and, if X is CH$_2$OY, oxidizing the compound of the formula I.

Step (a) of the process is preferably carried out in an inert organic solvent, particularly preferably in a halogenated solvent, such as, for example, 1,2-dichloroethane. The hydrolysis according to step (b) (saponification) can be carried out under alkaline, neutral or acidic conditions.

After the hydrolysis, N-phosphonomethylglycine should preferably be present in aqueous solution. The solvent used in step (a) has to be separated off prior to or after the hydrolysis. If it is present during the hydrolysis, it should not be consumed or decomposed, in particular for reasons of cost minimization. Accordingly, in one process variant, the solvent used in step (a) is partially or completely distilled off prior to the hydrolysis, i.e. prior to step (b), and the residue is hydrolyzed. According to a further preferred process variant, the hydrolysis is carried out in an aqueous/organic two-phase system. After the hydrolysis, the two phases are separated and worked up. N-Phosphonomethyl-glycine is found in the aqueous phase.

If the solvent is removed by distillation, the energy required for the process is very high; accordingly, removal by phase separation after hydrolysis is more economical. If, however, the solvent used is a chlorinated hydrocarbon, for example 1,2-dichloroethane, the stability of the solvent under the hydrolysis conditions is limited.

The insufficient stability of chlorinated hydrocarbons under hydrolysis conditions has been known for a long time. Thus, for example, H. Bahr and H. Zieler describe, in Angew. Chem. 43 (1930), 286, that, at temperatures above 150° C., dichloroethane is converted noticeably into ethylene glycol. DE 537 448 discloses the hydrolysis of dichloroethane into glycol using water at temperatures above 120° C., where the concentration of the hydrochloric acid that is formed is kept below 4%. DE 540 513 describes the preparation of glycol from cyanohydrins by hydrolysis in the presence of aqueous alkali metal hydroxide solution at 80–100° C.

From the given examples, it can be deduced that, in particular if neutral or alkaline hydrolysis conditions are used, decomposition of the solvent is likely. However, with a view to the costs of the starting materials, particular preference is given to neutral hydrolysis conditions, where the monoammonium salt is formed, and to alkaline hydrolysis conditions, where, for example, if aqueous sodium hydroxide solution is used, the monosodium salt of N-phosphonomethylglycine is formed. Both are readily soluble in water, and N-phosphonomethylglycine can be precipitated from their solutions by adding only one equivalent of acid. Thus, per mole of N-phosphonomethylglycine, only 1 mol of salt is formed. Acid hydrolysis requires a larger excess of acid, resulting in a higher salt load of the waste waters and higher costs for starting materials. On the other hand, owing to the tendency of the solvent to decompose, neutral and alkaline hydrolysis have to be carried out under very gentle conditions, resulting in considerably longer reaction times.

It is an object of the present invention to provide an improved process for preparing N-phosphonomethylglycine, both from an economical and an ecological point of view.

It is another object of the present invention to provide a process for preparing N-phosphonomethylglycine in which decomposition of the organic solvent is avoided and the product is obtained in high purity.

We have found that these objects are achieved by a process for preparing N-phosphonomethylglycine which comprises a) reacting a hexahydrotriazine derivative of the formula II

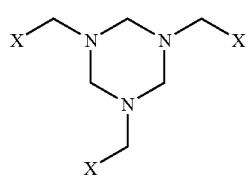

in which X is CN, COOZ, CONR$^1$R$^2$ or CH$_2$OY,

Y is H or a radical which is easily exchangeable for H;

Z is H, an alkali metal, an alkaline earth metal, C$_1$–C$_{18}$-alkyl or aryl which is unsubstituted or substituted by C$_1$–C$_4$-alkyl, NO$_2$ or OC$_1$–C$_4$-alkyl;

R$^1$ and R$^2$ may be identical or different and are H or C$_1$–C$_4$-alkyl, with a triacyl phosphite of the formula III

in which the radicals R$^3$, which may be identical or different, are C$_1$–C$_{18}$-alkyl or aryl which is unsubstituted or substituted by C$_1$–C$_4$-alkyl, NO$_2$ or OC$_1$–C$_4$-alkyl to give a compound of the formula I

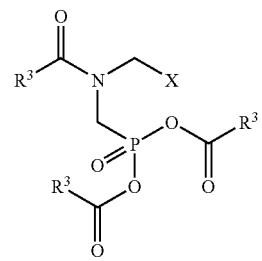

in which R$^3$ and X are as defined above, in an organic solvent, b) extracting the resulting reaction mixture with water or an aqueous solution of an acid or an aqueous solution of a base, c) separating the phases and d) hydrolyzing or further hydrolyzing the product contained in the aqueous phase.

After step (d), N-phosphonomethylglycine is obtained from the aqueous phase.

Any other useful and/or recyclable components contained in the aqueous phase are preferably likewise removed from the aqueous phase and, if appropriate, recycled into the process.

If X in formula II is CH$_2$OY, the product obtained after the hydrolysis still has to be oxidized.

Alkyl denotes a straight-chain or branched alkyl chain having preferably 1 to 8 carbon atoms and in particular 1 to 4 carbon atoms. Examples of alkyl are methyl, ethyl, n-propyl, isopropyl, n-butyl, isobutyl, sec-butyl, tert-butyl, n-hexyl, 2-ethylhexyl, etc.

Aryl is preferably phenyl or naphthyl.

X is preferably CN or COOZ.

z is preferably H, an alkali metal or C$_1$–C$_{18}$-alkyl.

If Y is a radical which can be readily exchanged for H, it is preferably an aliphatic or aromatic acyl radical or a C$_1$–C$_6$-alkyl group. The aliphatic acyl radical is preferably a C$_1$–C$_6$—CO radical, the aromatic acyl radical is preferably the benzoyl radical.

R$^1$ and R$^2$ preferably represent H.

The radical R$^3$ is particularly preferably an aryl radical which may be unsubstituted or substituted as stated above. Particularly suitable radicals R$^3$ are phenyl, p-tolyl and p-nitrophenyl.

The compounds of the formula II are known and can be prepared in a known manner or analogously to known processes, see, for example, the prior art mentioned above. It is possible, for example, to react an amine X—CH$_2$—NH$_2$ with a formaldehyde source such as aqueous Formalin solution or paraformaldehyde, for example by dissolving the primary amine in the aqueous Formalin solution. The desired hexahydrotriazine can then be obtained by crystallization or by evaporating the water. This process is described in DE-A-2645085, corresponding to U.S. Pat. No. 4,181,800, which is expressly incorporated herein in its entirety by way of reference.

The compound of the formula II in which X is CN can be obtained by Strecker synthesis, i.e. by reacting ammonia, hydrocyanic acid and a formaldehyde source. Such a process is described, for example, in U.S. Pat. No. 2,823,222, which is expressly incorporated herein in its entirety by way of reference.

The compounds of the formula III can be prepared by a number of processes. A first possibility is the reaction of a salt of a carboxylic acid $R^3COOH$ with a phosphorus trihalide, in particular phosphorus trichloride. The carboxylic acid salt used is preferably an alkali metal or alkaline earth metal salt, in particular the sodium, potassium or calcium salt, or the ammonium salt. This reaction can be carried out without using a solvent, and the reaction product obtained can be used directly for step (a). However, the reaction is preferably carried out in an inert organic solvent, in particular in an ether, such as dioxane, tetrahydrofuran, etc., a halogenated, in particular a chlorinated or fluorinated, organic solvent, such as dichloromethane, 1,2-dichloroethane, 1,2-dichloropropane, 1,1,1-trichloroethane, 1,1,2-trichloroethane, 1,1,2,2-tetra-chloroethane, chlorobenzene or 1,2-dichlorobenzene, an aliphatic or aromatic hydrocarbon, such as n-octane, toluene, xylene or nitrobenzene. Preference is given to using the same solvent as subsequently in step (a). Particular preference is given to using a chlorinated hydrocarbon.

The salt formed during the reaction, for example sodium chloride if phosphorus trichloride and the sodium salt of the carboxylic acid in question are used, can be removed after the reaction. If the salt obtained is ammonium chloride or another ammonium halide, the ammonia used can be recovered by making an aqueous solution of the salt alkaline (pH 11 to 14) using a srong base, for example aqueous sodium hydroxide solution, and the ammonia can then be stripped out in a customary manner. The ammonia obtained in this manner can be recycled after drying, for example by distillation in the liquid or gaseous state, or as an aqueous solution, and be used for preparing the ammonium salt of the carboxylic acid.

A further possibility of preparing the compounds of the formula III is the reaction of a carboxylic acid $R^3COOH$ with the phosphorus trihalide in the presence of an amine. The amines used are, in particular, aliphatic or cycloaliphatic di- or triamines, such as triethylamine, tributylamine, dimethylethylamine or dimethylcyclohexylamine, and also pyridine. In general, such a process is carried out in an organic solvent. Suitable solvents are listed above in connection with the first preparation option. Preference is given to using dioxane, 1,2-dichloropropane, 1,2-dichloroethane, nitrobenzene or toluene. If a solvent is used, the amine hydrochloride formed precipitates out and can be filtered off. If the amine hydrochlorides are treated with a strong base, for example with aqueous sodium hydroxide solution, the amines are released from the hydrochloride. Volatile amines can be recovered by distillation or extraction. Non-volatile amines can be obtained by extraction or, if a two-phase mixture is obtained during the release of the amine, by phase separation. Solid amines can be recovered by filtration. The recovered amines can, if appropriate after drying, be recycled into the process.

A further possibility of preparing the compounds of the formula III is the reaction of the carboxylic acid $R^3COOH$ with a phosphorus trihalide, in particular phosphorus trichloride, without addition of a base. In this reaction, it is necessary to remove the hydrogen halide formed from the reaction mixture. This can be carried out in a customary manner, for example by passing through an inert gas such as nitrogen. The hydrogen halide which is released can then, if an acid hydrolysis is intended, be used in the form of an aqueous solution for the hydrolysis in step (d).

Step (a) of the process according to the invention is carried out in an inert organic solvent which can be a water-miscible solvent but is preferably a water-immiscible solvent. Examples of suitable solvents are hydrocarbons, such as toluene or xylene, ethers, such as tetrahydrofuran, dioxane or dibutyl ether, nitrobenzene, etc. The step is particularly preferably carried out in a halogenated solvent, preferably a chlorinated and/or fluorinated aliphatic hydrocarbon, such as dichloromethane, 1,2-dichloroethane, 1,2-dichloropropane, 1,1,1-trichloroethane, 1,1,2,2-tetrachloroethane, chlorobenzene or 1,2-dichlorobenzene. Particular preference is given to 1,2-dichloroethane.

The reaction partners are expediently employed in substantially stoichiometric amounts. However, it is also possible to use an excess of, for example, up to 10% of one or the other reaction partner. The reaction temperature is generally in the range from $-10°$ C. to $140°$ C., preferably in the range from room temperature to $100°$ C. The reaction times required under these conditions are only short; in general, the reaction has substantially gone to completion after 10 to 30 min.

The compounds of the formula I obtained according to step (a) are useful intermediates for preparing N-phosphonomethylglycine. For the conversion into phosphonomethylglycine, the reaction mixture obtained in step (a) is initially subjected to an extraction (step (b)). This can be done under acidic, neutral or alkaline conditions. Here, the pH conditions may correspond to the desired conditions for the subsequent hydrolysis; however, the extraction may also be carried out in another pH range than that used for the subsequent hydrolysis. It is, for example, possible to extract in the acidic or neutral range and then to add a base and carry out the hydrolysis in the alkaline range.

The extraction is preferably carried out at a temperature of from room temperature to the reflux temperature of the reaction mixture, particularly preferably at at least $50°$ C. The phase transition of the phosphono compound I into the aqueous phase proceeds very rapidly: in the case of a phosphono compound I where X=CN and $R^3$=phenyl, on extraction into water at $50°$ C., after only 10 min over 95% of the entire phosphorous are already in the aqueous phase, at reflux temperature after 10 min almost 99%.

In general, extraction times of a few minutes, for example from 5 min, are sufficient, depending on the temperature. The extraction time is preferably at least 10 minutes, particularly preferably at least 1 hour. In particular in the case of extraction at low temperatures, a relatively long extraction time may be required, for example at least 2 hours.

During the extraction, at least some of the phosphono compound of the formula I is generally already partially hydrolyzed. Partial hydrolysis is to be understood as meaning that only some of the $R^3CO$ radicals contained in the product of step (a) are cleaved off. The extent of the hydrolysis depends on the phosphono compound in question and on the chosen extraction conditions. In the case of the compound I where X=CN and $R^3$=phenyl, after 10 minutes of extraction, 45 to 50% of the entire benzoic acid are already present in free form, depending on the extraction conditions.

The acids used for the extraction are in particular inorganic acids, such as hydrochloric acid, sulfuric acid or phosphoric acid. The alkaline extraction is generally carried out using an alkali metal hydroxide or alkaline earth metal hydroxide, in particular using sodium hydroxide or potassium hydroxide.

During the extraction, there is substantially no decomposition of the solvent mixture used in step (a), even if the solvent in question is a chlorinated hydrocarbon which has a particularly strong tendency to decompose.

The aqueous phase and the organic phase are then separated from one another (step (c)). This gives an organic phase which may contain impurities soluble therein, which can thus be separated from the product of value in a simple manner. The aqueous phase contains the product of step (a) and, if appropriate, its partially hydrolyzed product. Phase separation is carried out in a customary manner known to the person skilled in the art. The compound I and/or the partially hydrolyzed product present in the aqueous phase is then hydrolyzed (step (d)). Depending on the hydrolysis conditions desired, an acid or a base can be added to the aqueous phase. Owing to the high excess of acid required in the case of acid hydrolysis, the hydrolysis is preferably carried out under neutral or alkaline conditions.

To achieve the reaction temperatures desired, the hydrolysis is carried out under elevated pressure. Preferably, the reaction temperature during the hydrolysis is higher than that during the extraction. In general, the reaction temperature is at least 20° C., in particular at least 30° C., higher than that during the extraction. Preferred reaction temperatures are in the range from 100 to 180° C., particularly preferably from 130 to 150° C. The reaction time is preferably from about 5 minutes to 4 hours, particularly preferably from 10 minutes to 2 hours, very particularly preferably about 20 minutes.

For the hydrolysis, neutral or basic conditions are preferred. In the case of basic hydrolysis, the base is preferably employed in substantially equivalent amounts.

Acids and bases suitable for the hydrolysis are, in general, the acids and bases, respectively, mentioned above in connection with the extraction.

It is not necessary to adopt gentle hydrolysis conditions, since an organic solvent liable to decomposition is not present.

If X is $CH_2OY$, the product obtained after the hydrolysis still has to be oxidized. The material used is in particular a compound in which X is $CH_2OH$. The oxidation to give phosphonomethylglycine is carried out in a customary manner known to the person skilled in the art, for example by catalytic dehydrogenation under copper catalysis.

If X is $CH_2OY$ and Y is an acyl radical, the acyl radical is cleaved off during the hydrolysis of the product from step a), and the corresponding compound where $X=CH_2OH$ is formed. This is oxidized to give phosphonomethylglycine, as mentioned above.

If X is $CH_2OY$ and Y is an alkyl radical, under the conditions of an acid hydrolysis of the product from step a), the ether cleavage usually takes place at the same time. The resulting compound where $X—CH_2OH$ is, as mentioned above, oxidized to give phosphonomethylglycine.

After the hydrolysis has ended, the N-phosphonomethylglycine which, after the hydrolysis, is present in the form of a salt, is removed from the aqueous phase. This is preferably carried out by adjusting the pH in a suitable manner.

By adjusting the aqueous phase to a pH in the range from 0.5 to 2.0, in particular from 0.8 to 1.5, for example by adding an acid or a base, for example HCl, $H_2SO_4$ or NaOH, KOH, $Ca(OH)_2$, and, if appropriate, by concentrating the aqueous phase and/or adding a precipitation auxiliary, the phosphonomethylglycine is precipitated and isolated in a customary manner, for example by filtration. Suitable filtration auxiliaries are, preferably, water-miscible solvents, such as methanol, ethanol, isopropanol, acetone, etc. From the mother liquor, the solvents can be recovered by distillation and reused.

Ammonia formed during the hydrolysis, or any ammonium chloride formed, can be recycled into the process by, if appropriate, making the mixture alkaline and recovering the ammonia by stripping.

If required, the phosphonomethylglycine obtained can be decolorized in a suitable manner. This can be effected, for example, by treatment with small amounts of a decolorizing agent, for example oxidizing agents, such as perborate or $H_2O_2$, or adsorbents, such as activated carbon. The amount of decolorizing agent depends on the degree of discoloration and can be determined in a simple manner by the person skilled in the art. The treatment with the decolorizing agent can take place at any stage after the hydrolysis and in a customary manner. Expediently, the decolorizing agent is added prior to the precipitation of the phosphonomethylglycine.

In addition to N-phosphonomethylglycine, the reaction mixture formed during the hydrolysis contains further products and/or byproducts. The carboxylic acid $R^3COOH$ is formed during hydrolysis with an excess of acid or, in the case of neutral hydrolysis, directly or, in the case of basic hydrolysis, after acidification with a strong acid, preferably to a pH<0.5. The carboxylic acid is then removed in a customary manner, for example by filtering off the carboxylic acid which is precipitated in solid form, by distillation or by extraction with an organic solvent which is immiscible with the aqeueous phase. The carboxylic acid is obtained in high purity and can be reused without any problems for preparing the compound of the formula III. The organic solvent from step (a), too, can be recycled without any problems after the extraction of the compound I. However, in general, the solvent is first subjected to distillation, extraction, filtration and/or stripping to remove impurities. The process according to the invention or any step per se can be carried out continuously, batchwise or as a semi-batch process. The reaction vessels used are reaction vessels customary for such purposes, such as stirred tanks or tubular reactors, extraction columns, mixer-settlers or phase separators, if appropriate with upstream mixing devices or mixing elements built into the tubular reactor.

The process according to the invention is characterized by a simple process operation and inexpensive starting materials. The only waste produced is an inorganic chloride and the protective groups, the acyl radicals of the triacyl phosphite of the formula III can be recycled in a simple manner. The process gives N-phosphonomethylglycine in very short reaction times and high yields of more than 90%, starting with the hexahydrotriazine of the formula II.

By extracting the product of value into an aqueous phase prior to hydrolysis, decomposition of the organic solvent used in (a) is avoided. Gentle hydrolysis conditions are not required, and neutral or alkaline hydrolysis, which affords the monoammonium salt or the monosodium salt of N-phosphonomethylglycine and which is advantageous from an ecological point of view, can be employed without any problems. Both salts can be precipitated out by adding just one equivalent of acid, which reduces the salt load of the waste water and also the costs of the starting materials.

The examples below serve to illustrate the invention without limiting it.

EXAMPLE 1

Reaction of Triazine with Phosphite

In a 2 l stirred flask fitted with Teflon paddle stirrer and reflux condenser, 284 g of ammonium benzoate were initially charged in 1000 ml of 1,2-dichloroethane, and 91.5 g of phosphorus trichloride were added dropwise over a period of 30 min under an atmosphere of nitrogen. During the addition, the temperature increased to at most 360° C. Stirring was then continued at 25–36° C. for 30 min. The reaction mixture was filtered through a pressure nutsche, and the filtercake was, under nitrogen, washed twice with in each case 500 g of dichloroethane (2054 g of filtrate).

In a 2 l stirred flask fitted with Teflon paddle stirrer and reflux condenser, the filtrate was initially charged at room temperature, and the hexahydrotriazine 6(X=CN, 45.54 g) was added. With stirring, the mixture was heated to 80° C. over a period of 30 min and stirred at 80° C. for 30 min. The solution was allowed to cool and subsequently directly reacted further.

EXAMPLE 2

Extraction Step 150 g of the solution obtained according to example 1 (containing 0.051 mol of P) were stirred with 28 g of water or an aqueous solution, as stated in table 1. The phases were then separated and individually analyzed by P elemental analysis and quantitative HPLC for benzoic acid. The results given in the table were obtained.

TABLE 1

| Experiment No. | Aqueous solution | Reaction time | Reaction temperature | free benzoic acid % of total | free benzoic acid Aqueous phase | Proportion of P in the dichloroethane phase |
|---|---|---|---|---|---|---|
| 1 | water | 10 min | 50° C. | 45.7% | 7.3% | 3.8% |
| 2 | water | 2 h | 50° C. | 46.0% | 7.3% | 1.5% |
| 3 | water | 10 min | reflux | 46.7% | 7.2% | 1.3% |
| 4 | water | 2 h | reflux | 50.4% | 5.5% | 1.2% |
| 5 | 20% HCl | 10 min | reflux | 57.3% | 5.4% | 0.2% |
| 6 | 20% HCl | 2 h | reflux | 78.0% | 5.4% | 0.2% |

The columns under "free benzoic acid" indicate how many percent of the amount of benzoic acid theoretically added in the form of the phosphite are already present after the extraction dissolved in unbound form. The column aqueous phase indicates the proportion thereof that is still dissolved in the aqueous phase. The last column indicates which proportion of the total phosphorus remains in the organic phase after the extraction.

EXAMPLE 3

Hydrolysis Step Using Water

The aqueous phase obtained according to example 2, experiment No. 2, was heated further in a 10 ml pressure reactor. The reaction conditions are given in table 2. The reaction discharge was, at 50° C., extracted twice with toluene and then analyzed by quantitative HPLC and quantitative $^1$H-NMR analysis for phosphonomethylglycine. The results are listed in table 2. To isolate the N-phosphonomethylglycine, the reaction discharge was adjusted to pH=1.0 and the N-phosphonomethylglycine was filtered off and washed.

TABLE 2

| Reaction temperature | Reaction time | Yield analyzed | Yield isolated |
|---|---|---|---|
| 150° C. | 4 h | 39% | 30% |
| 150° C. | 1 h | 59% | 57% |
| 150° C. | 20 min | 75% | 72% |
| 140° C. | 1 h | 74% | 71% |
| 130° C. | 1 h | 61% | 55% |

EXAMPLE 4

Hydrolysis Step Using Alkaline Conditions 0.051 mol of 50% strength aqueous sodium hydroxide solution was added to the aqueous phase obtained according to example 2, experiment No. 2, and the reaction mixture was heated further in a pressure reactor. The reaction conditions are given in table 3. The reaction discharge was analyzed by quantitative HPLC and quantitative $^1$H-NMR analysis for phosphonomethylglycine (yield of the synthesis). The results are compiled in table 3. To isolate the phosphonomethylglycine, the mixture was extracted three times with 1,2-dichloroethane at 60° C. and pH=2.5, the pH was then adjusted to pH=1.0, a little methanol was added, the mixture was stirred at 40° C. for another 3 hours, the phosphonomethyl-glycine was filtered off and the residue was washed with ice water.

TABLE 3

| Reaction temperature | Reaction time | Yield in synthesis | Yield isolated |
|---|---|---|---|
| 180° C. | 20 min | 43% | 24% |
| 150° C. | 2 h | 87% | 81% |
| 150° C. | 30 min | 90% | 85% |
| 150° C. | 15 min | 92% | 88% |
| 140° C. | 1 h | 71% | 60% |
| 130° C. | 1 h | 50% | 38% |

We claim:

1. A process for preparing N-phosphonomethylglycine which comprises
   a) reacting a hexahydrotriazine derivative of the formula II

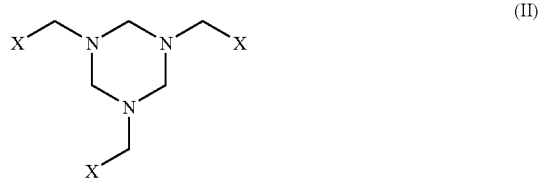

(II)

in which X is CN, COOZ, CONR$^1$R$^2$ or CH$_2$OY,
Y is H or a radical which is easily exchangeable for H;
Z is H, an alkali metal, an alkaline earth metal, C$_1$–C$_{18}$-alkyl or aryl which is unsubstituted or substituted by C$_1$–C$_4$-alkyl, NO$_2$ or OC$_1$–C$_4$-alkyl;
R$^1$ and R$^2$ may be identical or different and are H or C$_1$–C$_4$-alkyl,
with a triacyl phosphite of the formula III

P(OCOR$^3$)$_3$ (III)

in which the radicals $R^3$, which may be identical or different, are $C_1$–$C_{18}$-alkyl or aryl which is unsubstituted or substituted by $C_1$–$C_4$-alkyl, $NO_2$ or $OC_1$–$C_4$-alkyl in an organic solvent,
b) extracting the resulting reaction mixture with water or an aqueous solution of an acid or an aqueous solution of a base,
c) separating the phases and
d) hydrolyzing the product contained in the aqueous phase.

2. A process as claimed in claim 1 where, after step (d), the N-phosphonomethylglycine is obtained from the aqueous phase.

3. A process as claimed in claim 2 where the N-phosphonomethyl-glycine is precipitated out by adjusting the pH to a value in the range from 0.5 to 2.0.

4. A process as claimed in any of claims 1 to 3 where, if X in compound II is $CH_2OY$, the product obtained after step (d) is oxidized.

5. A process as claimed in any of claims 1 to 4 where the extraction according to step (b) is carried out at a temperature of from room temperature to the reflux temperature of the mixture.

6. A process as claimed in any of claims 1 to 5 in which the hydrolysis according to step (d) is carried out under neutral or alkaline conditions.

7. A process as claimed in any of claims 1 to 6 where the hydrolysis according to step (d) is carried out at a temperature higher than that of the extraction according to step (b).

8. A process as claimed in claim 7 where the temperature in step (d) is in the range from 100° C. to 180° C.

9. A process as claimed in any of claims 1 to 8 where the solvent used is a chlorinated hydrocarbon, preferably 1,2-dichloroethane.

10. A process as claimed in any of claims 1 to 9 where the triacyl phosphite of the formula III used is benzoyl phosphite.

11. A process as claimed in any of claims 1 to 10 where X is CN or COOZ.

12. A process as claimed in any of claims 1 to 11 where $R^3$ is phenyl which is unsubstituted or substituted by $C_1$–$C_4$-alkyl, $NO_2$ or $OC_1$–$C_4$-alkyl or is $CH_3$.

13. A process as claimed in any of claims 1 to 12 where the compounds of the formulae II and III are employed in substantially equivalent amounts.

14. A process as claimed in any of claims 1 to 13 where the solvent from step (a) is recovered after step (c) and recycled.

* * * * *

UNITED STATES PATENT AND TRADEMARK OFFICE
CERTIFICATE OF CORRECTION

PATENT NO. : 7,145,034 B2
APPLICATION NO. : 10/481579
DATED : December 5, 2006
INVENTOR(S) : Wulff et al.

It is certified that error appears in the above-identified patent and that said Letters Patent is hereby corrected as shown below:

On the Title page, item "Foreign Patent Documents":
 "DE 118 435" should read -- DD 118 435 --
 "DE 141 929" should read -- DD 141 929 --

In Claim 4, col. 13, line 18: "any of claims 1 to 3" should read -- claim 1 --

In Claim 5, col. 13, line 21: "any of claims 1 to 4" should read -- claim 1 --

In Claim 6, col. 13, line 25: "any of claims 1 to 5" should read -- claim 1 --

In Claim 7, col. 14, line 1: "any of claims 1 to 6" should read -- claim 1 --

In Claim 9, col. 14, line 7: "any of claims 1 to 8" should read -- claim 1 --

In Claim 10, col. 14, line 10: "any of claims 1 to 9" should read -- claim 1 --

In Claim 11, col. 14, line 14: "any of claims 1 to 10" should read -- claim 1 --

In Claim 12, col. 14, line 16: "any of claims 1 to 11" should read -- claim 1 --

In Claim 13, col. 14, line 19: "any of claims 1 to 12" should read -- claim 1 --

In Claim 14, col. 14, line 23: "any of claims 1 to 13" should read -- claim 1 --

Signed and Sealed this

Seventeenth Day of April, 2007

JON W. DUDAS
*Director of the United States Patent and Trademark Office*